United States Patent [19]

Nishibori et al.

[11] Patent Number: 6,075,142
[45] Date of Patent: Jun. 13, 2000

[54] PROCESS FOR PRODUCTION OF TRIS (TRIBROMOPHENOXY)-S-TRIAZINE

[75] Inventors: Setsuo Nishibori, Shiga; Hideto Kondo, Kyoto, both of Japan

[73] Assignee: Dai-Ichi Kogyo Seiyaku Co., Ltd., Kyoto, Japan

[21] Appl. No.: 09/318,094

[22] Filed: May 25, 1999

Related U.S. Application Data

[63] Continuation of application No. 08/726,035, Oct. 7, 1996, Pat. No. 5,907,040, which is a continuation of application No. 08/266,915, Jun. 24, 1994, abandoned.

[30] Foreign Application Priority Data

Jul. 8, 1993 [JP] Japan .................................... 5-168834
Jul. 8, 1993 [JP] Japan .................................... 5-168835

[51] Int. Cl.$^7$ .................................................. C07D 251/30
[52] U.S. Cl. ............................................................. 544/219
[58] Field of Search .............................................. 544/219

[56] References Cited

U.S. PATENT DOCUMENTS 5,907,040  5/1999  Nishibori ................................ 544/219

*Primary Examiner*—John M. Ford
*Attorney, Agent, or Firm*—Jordan and Hamburg LLP

[57] ABSTRACT

A process for producing tris(tribromophenoxy)-s-triazine. The process is characterized in that cyanuric chloride and an aqueous tribromophenolate solution are subjected to reaction in the presence of a tertiary amine. According to this process, the reaction goes to completion in a short time and the yield and purity of the product are high.

3 Claims, No Drawings

PROCESS FOR PRODUCTION OF TRIS (TRIBROMOPHENOXY)-S-TRIAZINE

This is a continuation, of application Ser. No. 08/726,035, filed Oct. 7, 1996, now U.S. Pat. No. 5,907,040, which is a continuation of application Ser. No. 08/266,915, filed Jun. 24, 1994 now abandoned.

BACKGROUND OF THE INVENTION

This invention relates to a process for producing tris (tribromophenoxy)-s-triazine.

Tris(tribromophenoxy)-s-triazine compounds as such are known from French Patent 1566675. It is also known from U.S. Pat. No. 3,843,650 and Japanese Kokai Patent Publication No. 47-25232 that these compounds have very satisfactory properties for application as flame retardant additives to synthetic resins. However, tris(tribromophenoxy)-s-triazine compounds as described in French Patent 1566675 were of low purity and could be made available only in low yield.

The technology for production of tris(tribromophenoxy)-s-triazine, thus far known from Japanese Kokai Patent Publication No. 47-25232 and U.S. Pat. No. 3,843,650, comprises dissolving cyanuric chloride in a ketone or cyclic ether solvent and adding an aqueous or ethanolic solution of a tribromophenolate. An alternative process, disclosed in JP Kokai No. 53-116390, comprises an alkali treatment in the presence of a phase transfer catalyst in a heterogeneous solvent system consisting of water and an organic solvent.

However, in the production system employing a hydrophilic solvent, solvent recovery entails the azeotropic inclusion of water in the recovered solvent and this water can hardly be removed from the solvent. If the recovered solvent is reused in the reaction, the charge cyanuric chloride is hydrolyzed and the resulting hydrolyzate contaminates the reaction system. This causes a decreased purity of the product compound and, when such product is added to synthetic resin, both the physical properties and flame resistance of the resin are adversely affected.

In the production system employing a non-hydrophilic solvent, as described in Japanese Kokai Patent Publication No. 3-34972, tris(tribromophenoxy)-s-triazine of high purity can be obtained in high yield but prolonged aging was essential for carrying the reaction to completion. However, when the tribromophenolate-cyanuric chloride reaction system involves an extended period of aging, cyanuric chloride is hydrolyzed by water in its reaction with the tribromophenolate so that the product tris(tribromophenoxy)-s-triazine cannot be of high purity. To overcome this disadvantage, in the production process employing a non-hydrophilic solvent, it might be contemplated to use a phase transfer catalyst in an increased amount. However, the phase transfer catalyst is so expensive that it is uneconomical to use it in a large amount and actually an increase in the amount of a phase transfer catalyst contributes little to a reduction in reaction time.

SUMMARY OF THE INVENTION

The object of this invention is to provide a process for producing tris(tribromophenoxy)-s-triazine of high purity in a reduced reaction time and in high yield.

The inventors of this invention discovered that when a tertiary amine is used as the catalyst, the reaction goes to completion in a short time substantially without aging. They further found a production process in which hydrolysis of the charge cyanuric chloride can be minimized by reducing the influence of water on the cyanuric chloride as far as possible.

This invention is directed to a process for producing tris(tribromophenoxy)-s-triazine characterized in that cyanuric chloride and an aqueous solution of a tribromophenolate are subjected to reaction in the presence of a tertiary amine.

While optionally a phase transfer catalyst can also be used in the reaction of this invention, it can be used only in a reduced amount compared with the conventional processes employing a phase transfer catalyst alone.

DETAILED DESCRIPTION OF THE PREFERRED EMBODIMENT (1) Preparation of a Tribromophenolate Preparation of a tribromophenolate comprises dissolving an alkali, for example sodium hydroxide or potassium hydroxide, in water, adding tribromophenol to the resulting aqueous solution after cooling, and allowing the tribromophenol to dissolve completely at elevated temperature or room temperature. The preferred molar ratio of tribromophenol to alkali is 1:1–1.2.

A highly concentrated aqueous tribromophenolate solution of not less than 50% (weight %; the same applies hereinafter) can be prepared by adding a non-hydrophilic solvent in the above procedure. When such a highly concentrated aqueous tribromophenolate solution is used in the reaction with cyanuric chloride, the productivity, i.e. output per unit reactor capacity, of tris(tribromophenoxy)-s-triazine is enhanced.

The concentration of an aqueous tribromophenolate solution as referred to throughout this specification is the concentration in terms of tribromophenol. Thus, the concentration of tribromophenol relative to water can be calculated by means of the following equation.

$$\text{Concentration (\%)} = \frac{\text{Weight of tribromophenol}}{\text{Weight of tribromophenol} + \text{weight of water}} \times 100$$

Preparation of such a highly concentrated aqueous tribromophenolate solution comprises dissolving an alkali, for example sodium hydroxide or potassium hydroxide, in water, adding a non-hydrophilic solution to the resulting aqueous solution after cooling, further adding tribromophenol, and allowing the tribromophenol to dissolve completely at an elevated temperature or room temperature.

Referring to workability, the preparation of a tribromophenolate can be facilitated by adding a non-hydrophilic solvent beforehand. Moreover, the aqueous tribromophenolate solution so prepared has a high specific gravity so that the aqueous layer separates readily from the non-hydrophilic solvent layer. The tribromophenolate is insoluble in the non-hydrophilic solvent. Therefore, by withdrawing the separated non-hydrophilic solvent and dissolving a fresh supply of tribromophenol therein, a large quantity of the tribromophenolate can be prepared even when the available reactor capacity is limited. The withdrawn non-hydrophilic solvent can be used as it is as the reaction solvent. In terms of productivity, too, since a large quantity of tribromophenolate can be produced per unit reactor capacity, the output of tris(tribromophenoxy)-s-triazine per reaction can be increased. Furthermore, the amount of water finding its way into the reactor is so small that the hydrolysis of cyanuric chloride can be held at a minimum and the reaction can be conducted in dispersion, not requiring to completely dissolve cyanuric chloride in the non-hydrophilic solvent. In addition, when cyanuric chloride can be so handled, its powder can be directly added to the tribromophenolate solution for reaction.

(2) Cyanuric Chloride

For use in this invention, cyanuric chloride in the form of bulk powder can be directly subjected to the reaction. Alternatively, it can be dissolved or dispersed in the non-hydrophilic solvent before use.

(3) Solvent

The solvent for use in this invention is not critical in type only if it is non-hydrophilic. Thus, the solvent includes halogenated hydrocarbons such as methylene chloride, chloroform, carbon tetrachloride, trichloroethylene, perchloroethylene, tetrachloroethylene, etc., aromatic hydrocarbons such as benzene, toluene, xylene, etc., saturated hydrocarbons such as hexane etc., and halogen-substituted aromatic hydrocarbons such as chlorobenzene etc., among others. The preferred are solvents in which Cyanuric chloride is well soluble, for example halogenated hydrocarbons such as chloroform and methylene chloride. For dissolving cyanuric chloride, two or more of these solvents can be used in combination. Moreover, the solvent for use in dissolving or dispersing cyanuric chloride may be different from the non-hydrophilic solvent for use in dissolving the tribromophenolate in water at a high concentration level. For dissolving the tribromophenolate, too, two or more non-hydrophilic solvents can be used in combination.

The solvent recovered by distillation can be reused as it is, or if necessary, the water contained can be removed with a desiccating agent or the like. There is no particular limit to the amount of the solvent used for dissolving or dispersing cyanuric chloride but it is preferable to employ not less than 2.0 parts by weight of the solvent to each part by weight of cyanuric chloride. If the proportion of the solvent is less than the above limit, the reaction procedure may be interfered with. Since the non-hydrophilic solvent used for the preparation of said highly concentrated aqueous tribromophenolate solution can be withdrawn from the reactor top after preparation of the tribromophenolate, its amount is not particularly critical but is preferably not less than 0.1 part by weight relative to tribromophenol.

(4) Tertiary Amine

The tertiary amine which is and can be used in this invention includes trimethylamine, triethylamine, tripropylamine, tributylamine, triamylamine, trihexylamine, trioctylamine, tribenzylamine, diethylbenzylamine, triphenylamine, pyridine, tetramethylethylenediamine and so on. Preferred are highly water-soluble tertiary amines. The level of addition of the amine is 0.01–5.0% based on cyanuric chloride.

The tertiary amine can be added to the tribromophenolate solution or the cyanuric chloride solution beforehand. Furthermore, this addition can be done either prior to the reaction, after the reaction or during the aging stage. Where the tertiary amine is added after the reaction or in the course of aging, the temperature of addition is preferably not exceeding whichever is lower of the boiling point of the tertiary amine and that of the non-hydrophilic solvent.

(5) Phase Transfer Catalyst

The phase transfer catalyst which is used where necessary in this invention includes salts of quaternary phosphorus compounds such as triphenylbenzylphosphonium chloride, triphenylethylphosphonium bromide, butyltriphenylphosphonium chloride, phenacetyltriphenyiphosphonium chloride, hexyltriphenylphosphonium bromide, octyltriphenylphosphonium bromide, tetraphenylphosphonium bromide, 2-methylbenzyltriphenylphosphonium bromide, methyltriphenylphosphonium iodide, phenacetyltriphenylphosphonium chloride, allyltriphenylphosphonium bromide, etc.; salts of quaternary nitrogen compounds such as tetramethylammonium chloride, tetramethylammonium bromide, tetraethylammonium chloride, tetraethylammonium bromide, tetrapropylammonium chloride, tetrapropylammonium bromide, tetrabutylammonium chloride, tetrabutylammonium bromide, trimethylphenyammonium chloride, trimethylphenylammonium bromide, triethylphenylammonium chloride, triethylphenylammonium bromide, trimethylbenzylammonium chloride, trimethylbenzylammonium bromide triethylbenzylammonium chloride, triethylbenzylammonium bromide, tributylbenzylammonium chloride, tributylbenzylammonium bromide, dimethylbenzylphenylammonium chloride, dimethylbenzylphenylammonium bromide, tetrabenzylammonium chloride, tetrabenzylammonium bromide, tribenzylphenylammonium chloride, tribenzylphenylammonium bromide, trimethylcyclohexylammonium chloride, trimethylcyclohexylammonium bromide, tributylcyclohexylammonium chloride, tributylcyclohexylammonium bromide, trioctylmethylammonium chloride, tributylmethylartmisonium bromide, trimethyl-n-laurylammonium chloride, trimethyl-n-laurylammonium bromide, n-laurylpyridinium chloride, n-laurylpyridinium bromide, n-stearylpyridinium chloride, n-stearylpyridinium bromide, etc.; crown ethers such as 15-crown-5, 18-crown-6, dibenzo-18-crown-6, dicyclohexyl-18-crown-6, dibenzo-24-crown-8, dicyclohexyl-24-crown-8 and so on.

The level of addition based on cyanuric chloride is 0.1–10.0%, preferably 2.0–5.0%.

The phase transfer catalyst can be added to the tribromophenolate solution beforehand or similarly to the cyanuric chloride solution.

(6) Production Process

An exemplary production process according to this invention comprises preparing an aqueous tribromophenolate solution and dripping this aqueous solution to a dispersion or solution of cyanuric chloride and tertiary amine in a non-hydrophilic solvent or adding said tertiary amine and a powder of cyanuric chloride to said aqueous solution. The preferred molar ratio of cyanuric chloride to tribromophenol is 1:2.94–3.60. Where both a tertiary amine and a phase transfer catalyst are employed, an exemplary procedure comprises preparing an aqueous tribromophenolate solution, adding a tertiary amine thereto and dripping the mixture to a solution or dispersion of cyarnuric chloride and phase transfer catalyst in a non-hydrophilic solvent or adding said phase transfer catalyst, said tertiary amine and a powder of cyanuric chloride to the aqueous tribromophenolate solution. After the above dripping or addition, the reaction system is aged where necessary and the non-hydrophilic solvent is removed from the reaction system at atmospheric or subatmospheric pressure. In this manner, tris (tribromophenoxy)-s-triazine of high purity can be obtained.

The reaction temperature is not so critical but when the recovered solvent was used in the procedure for dropwise addition of the aqueous tribromophenolate solution to a solution or dispersion of cyanuric chloride, the reaction system is preferably cooled to 10° C. or below up to immediately before the dripping of the aqueous tribromophenolate solution for inhibiting the hydrolysis of cyanuric chloride. After the dripping has started, the reaction temperature may be increased up to the boiling point of the solvent. Preferably, however, the dropwise addition is carried out at a low temperature to minimize the hydrolysis of cyanuric chloride.

The phase transfer catalyst is a catalyst which is capable of catalyzing the reaction between the cyanuric chloride dissolved in a non-hydrophilic solvent and the tribromophenolate dissolved in water, i.e. in a heterogeneous solvent system consisting of water and a non-hydrophilic solvent. In case the tertiary amine and phase transfer catalyst are used in combination in the process of this invention, the phase transfer catalyst converts the water-soluble tribromophenolate to the oil-soluble tribromophenolate and the latter finds its way into the non-hydrophilic solvent and reacts with the cyanuric chloride there. After the reaction, the phase transfer catalyst is reused for the conversion of water-soluble tribromophenolate to oil-soluble tribromophenolate and the reaction is repeated.

(7) Additives

In this invention, various additives such as reducing agents, stabilizers and defoaming agents can be employed.

In particular, a reducing agent serves to inhibit the oxidative polymerization of tribromophenol. The reducing agent which can be used includes, among others, phenol compounds such as phenol, bromophenol, dibromophenol, 2,6-di-t-butyl-4-methylphenol (BHT), etc., salts of sulfurous acid such as ammonium sulfite, potassium sulfite, sodium sulfite, sodium hydrogensulfite, etc., and sulfides such as sodium sulfide, ammonium sulfide, potassium sulfide and so on. The preferred level of addition of said reducing agent based on 100 parts by weight of tribromophenol is 0.01–1.0 parts by weight.

The process of this invention for the production of tris(tribromophenoxy)-s-triazine is more advantageous than the prior art processes in that the reaction goes to completion in a reduced time and insures a higher product purity and a higher product yield.

The following examples are intended to illustrate this invention in further detail and should by no means be construed as defining the scope of the invention.

EXAMPLE 1

A 500 ml reactor equipped with a stirrer, condenser, thermometer and drip funnel was charged with 130 g of methylene chloride and 20 g (0.108 mol) of cyanuric chloride, followed by addition of 0.8 g of triethylamine to the resulting solution or dispersion.

Another 500 ml reactor equipped with a stirrer, condenser and thermometer was charged with 130 g of water and 13.6 g (0.34 mol) of sodium hydroxide and the solution was cooled to a temperature not exceeding 10° C. Then, 110 g (0.33 mol) of 2,4,6-tribromophenol (TBP) was added and dissolved. The tribromophenolate solution (concentration of TBP=46%) thus obtained was added dropwise to the above cyanuric chloride solution at a temperature of 3–30° C. After completion of the dropwise addition, the reaction mixture was aged under reflux.

The reaction mixture was sampled at completion of dropwise addition (0.0 hour) and after 0.5 hour, 1.0 hour, 1.5 hours, 2.0 hours and 2.5 hours of aging. Each sample was poured in methanol and the precipitate was recovered by filtration and dried. The melting point was then measured with a Mettler melting point apparatus.

The results are shown in Table 1.

The concentration of TBP (2,4,6-tribromophenol) was calculated by means of the following equation.

$$\text{Concentration of } TBP\ (\%) = \frac{\text{Weight of } TBP\ (g)}{\text{Weight of } TBP\ (g) + \text{weight of water (g)}} \times 100$$

COMPARATIVE EXAMPLE 1

A 500 ml reactor equipped with a stirrer, condenser, thermometer and drip funnel was charged with 130 g of methylene chloride and 20 g (0.108 mol) of cyanuric chloride, followed by addition of 0.6 g of triphenylethylphosphonium bromide to the resulting solution or dispersion.

Another 500 ml reactor equipped with a stirrer, condenser and thermometer was charged with 130 g of water and 13.6 g (0.34 mol) of sodium hydroxide and the solution was cooled to a temperature not exceeding 10° C. Then, 110 g (0.33 mol) of 2,4,6-tribromophenol was added and dissolved. After cooling, the tribromophenolate solution (concentration of TBP=46%) thus obtained was added dropwise to the above cyanuric chloride solution at a temperature of 3–30° C. After completion of the dropwise addition, the reaction mixture was aged under reflux.

The reaction mixture was sampled at completion of dropwise addition (0.0 hour) and after 0.5 hour, 1.0 hour, 1.5 hours, 2.0 hours and 2.5 hours of aging. Each sample was poured in methanol and the precipitate was recovered by filtration and dried. The melting point was then measured with a Mettler melting point apparatus.

The results are shown in Table 1.

COMPARATIVE EXAMPLE 2

A 500 ml reactor equipped with a stirrer, condenser, thermometer and drip funnel was charged with 130 g of methylene chloride and 20 g (0.108 mol) of cyanuric chloride, followed by addition of 0.6 g of triphenylethylphosphonium bromide to the resulting solution or dispersion.

Another 500 ml reactor equipped with a stirrer, condenser and thermometer was charged with 130 g of water and 13.6 g (0.34 mol) of sodium hydroxide and the solution was cooled to a temperature not exceeding 10° C. Then, 110 g (0.33 mol) of 2,4,6-tribromophenol was added and dissolved. After cooling, the tribromophenolate solution (concentration of TBP=46%) thus obtained was added dropwise to the above cyanuric chloride solution at a temperature of 3° C.—reflux temperature. After completion of the dropwise addition, the reaction mixture was aged under reflux.

The reaction mixture was sampled at completion of dropwise addition (0.0 hour) and after 0.5 hour, 1.0 hour, 1.5 hours, 2.0 hours and 2.5 hours of aging. Each sample was poured in methanol and the precipitate was recovered by filtration and dried. The melting point was then measured with a Mettler melting point apparatus.

The results are shown in Table 1.

TABLE 1

|  |  | Melting point (° C.) Aging time (Hr) | | | | |
|---|---|---|---|---|---|---|
|  |  | 0.0 | 0.5 | 1.0 | 1.5 | 2.0 | 2.5 |
| Example | 1 | 225 | 230 | 230 | 230 | 230 | 230 |
| Comparative Example | 1 2 | 221 219 | 218 210 | 216 212 | 218 212 | 220 218 | 227 225 |

EXAMPLE 2

A 500 ml reactor equipped with a stirrer, condenser, thermometer and drip funnel was charged with 160 g of methylene chloride and 25 g (0.136 mol) of cyanuric chloride, followed by addition of 1.0 g of 30% aqueous solution of trimethylamine to the resulting solution or dispersion.

Another 500 ml reactor equipped with a stirrer, condenser and thermometer was charged with 150 g of water and 17.1 g (0.43 mol) of sodium hydroxide and the solution was cooled to a temperature not exceeding 10° C. Then, 136 g (0.41 mol) of 2,4,6-tribromophenol was added and dissolved. The tribromophenolate solution (concentration of TBP=48%) thus obtained was added dropwise to the above cyanuric chloride solution at a temperature of 3–30° C. After completion of the dropwise addition, the reaction mixture was aged under reflux for 30 minutes. After aging, the methylene chloride was distilled off at atmospheric pressure.

The product was recovered by filtration and dried to provide white crystals of tris(tribromophenoxy)-s-triazine.

The results are shown in Table 2.

EXAMPLE 3

A 500 ml reactor equipped with a stirrer, condenser, thermometer and drip funnel was charged with 160 g of methylene chloride and 25 g (0.136 mol) of cyanuric chloride, followed by addition of 1.0 g of 30% aqueous solution of trimethylamine to the resulting isolution or dispersion.

Another 500 ml reactor equipped with a stirrer, condenser and thermometer was charged with 150 g of water, 17.1 g (0.43 mol) of sodium hydroxide and 0.07 g of sodium sulfite and the solution was cooled to a temperature not exceeding 10° C. Then, 136 g (0.41 mol) of 2,4,6-tribromophenol was added and dissolved. The tribromophenolate solution (concentration of TBP=48%) thus obtained was added dropwise to the above cyanuric chloride solution at a temperature of 3–30° C. After completion of the dropwise addition, the reaction mixture was aged under reflux for 30 minutes. After aging, the methylene chloride was distilled off at atmospheric pressure.

The product was recovered by filtration and dried to provide white crystals of tris(tribromophenoxy)-s-triazine.

The results are shown in Table 2.

EXAMPLE 4

A 500 ml reactor equipped with a stirrer, condenser and thermometer was charged with 150 g of water, 17.1 g (0.43 mol) of sodium hydroxide and 0.07 g of sodium sulfite and the solution was cooled to a temperature not exceeding 10° C. Then, 136 g (0.41 mol) of 2,4,6-tribromophenol was added and dissolved. The solution was cooled to a temperature not exceeding 10° C., followed by addition of 160 g of methylene chloride and 1.0 g of 30% aqueous solution of trimethylamine. To the tribromophenolate solution (concentration of TBP=48%) thus obtained was added 25 g (0.136 mol) of cyanuric chloride powder at a reaction temperature of 3–30° C. After completion of the addition, the reaction mixture was aged under reflux for 30 minutes. After aging, the methylene chloride was distilled off at atmospheric pressure.

The product was recovered by filtration and dried to provide white crystals of tris(tribromophenoxy)-s-triazine.

The results are shown in Table 2.

COMPARATIVE EXAMPLE 3

A 500 ml reactor equipped with a stirrer, condenser, thermometer and drip funnel was charged with 160 g of methylene chloride and 25 g (0.136 mol) of cyanuric chloride, followed by addition of 0.8 g of triethylbenzylammonium chloride to the resulting solution or dispersion.

Another 500 ml reactor equipped with a stirrer, condenser and thermometer was charged with 150 g of water and 17.1 g (0.43 mol) of sodium hydroxide and the solution was cooled to a temperature not exceeding 10° C. Then, 136 g (0.41 mol) of 2,4,6-tribromophenol was added and dissolved. After cooling, the tribromophenolate solution (concentration of TBP=48%) thus obtained was added dropwise to the above cyanuric chloride solution at a temperature of 3–30° C. After completion of the dropwise addition, the reaction mixture was aged under reflux for 30 minutes. After aging, the methylene chloride was distilled off at atmospheric pressure.

The product was recovered by filtration and dried to provide white crystals of tris(tribromophenoxy)-s-triazine.

The results are shown in Table 2.

TABLE 2

|  | Example 2 | Example 3 | Example 4 | Comparative Example 3 |
|---|---|---|---|---|
| Yield (g) | 138.9 | 140.5 | 140.6 | 124.2 |
| Yield (%) | 96 | 97 | 97 | 86 |
| Melting point (° C.) | 230.0 | 230.0 | 230.1 | 219.8 |
| Heat resistance (APHA)* | 40 | 30 | 30 | 500 |

*A sample, 5 g, is taken in & Pyrex test tube, which is then placed in an aluminum block bath at a constant temperature of 300° C. and allowed to stand for 20 minutes. After cooling, methylene chloride is added to prepare a 2 w/v % solution. The color of the methylene chloride solution is measured against the APHA colorimetric tube (ASTM-D 1209).

EXAMPLE 5

A 500 ml reactor equipped with a stirrer, condenser, thermometer and drip funnel was charged with 150 g of methylene chloride and 50 g (0.271 mol) of cyanuric chloride, followed by addition of 1.0 g of 30% aqueous solution of trimethylamine to the resulting solution or dispersion.

Another 500 ml reactor equipped with a stirrer, condenser and thermometer was charged with 96 g of water and 34.2 g (0.86 mol) of sodium hydroxide and the solution was cooled to a temperature not exceeding 10° C. Then, 130 g of methylene chloride, i.e. the reaction solvent, and 272 g (0.82 mol) of 2,4,6-tribromophenol were added and dissolved. The tribromophenolate solution (concentration of TBP= 74%) thus obtained was added dropwise to the above cyanuric chloride solution at a temperature of 3–30° C. After completion of the dropwise addition, the reaction mixture was aged under reflux for 30 minutes. After aging, the methylene chloride was distilled off at atmospheric pressure.

The product was recovered by filtration and dried to provide white crystals of tris(tribromophenoxy)-s-triazine.

The results are shown in Table 3.

EXAMPLE 6

A 500 ml reactor equipped with a stirrer, condenser, thermometer and drip funnel was charged with 150 g of methylene chloride and 50 g (0.271 mol) of cyanuric chloride, followed by addition of 1.0 g of 30% aqueous solution of trimethylamine to the resulting solution or dispersion.

Another 500 ml reactor equipped with a stirrer, condenser and thermometer was charged with 96 g of water, 34.2 g (0.86 mol) of sodium hydroxide and 0.14 g of sodium sulfite and the solution was cooled to a temperature not exceeding 10° C. Then, 130 g of methylene chloride, i.e. the reaction solvent, and 272 g (0.82 mol) of 2,4,6-tribromophenol were added and dissolved. The tribromophenolate solution (concentration of TBP=74%) thus obtained was added dropwise to the above cyanuric chloride solution at a temperature of 3–30° C. After completion of the dropwise addition, the reaction mixture was aged under reflux for 30 minutes. After aging, the methylene chloride was distilled off at atmospheric pressure.

The product was recovered by filtration and dried to provide white crystals of tris(tribromophenoxy)-s-triazine.

The results are shown in Table 3.

EXAMPLE 7

A 500 ml reactor equipped with a stirrer, condenser and thermometer was charged with 96 g of water, 34.2 g (0.86 mol) of sodium hydroxide and 0.14 g of sodium sulfite and the solution was cooled to a temperature not exceeding 10° C. Then, 130 g of methylene chloride, i.e. reaction solvent, and 272 g (0.82 mol) of 2,4,6-tribromophenol were added and dissolved. The solution was cooled to a temperature not exceeding 10° C., followed by addition of 1.0 g of 30% aqueous solution of trimethylamine and 150 g of methylene chloride. To the tribromophenolate solution (concentration of TBP=74%) thus obtained was added 50 g (0.271 mol) of cyanuric chloride powder at a reaction temperature of 3–30° C. After completion of the addition, the reaction mixture was aged under reflux for 30 minutes. After aging, the methylene chloride was distilled off at atmospheric pressure.

The product was recovered by filtration and dried to provide white crystals of tris(tribromophenoxy)-s-triazine.

The results are shown in Table 3.

COMPARATIVE EXAMPLE 4

A 500 ml reactor equipped with a stirrer, condenser, thermometer and drip funnel was charged with 160 g of methylene chloride and 25 g (0.136 mol) of cyanuric chloride, followed by addition of 0.8 g of tetrabutylammonium bromide to the resulting solution or dispersion.

Another 500 ml reactor equipped with a stirrer, condenser and thermometer was charged with 150 g of water and 17.1 g (0.43 mol) of sodium hydroxide and the solution was cooled to a temperature not exceeding 10° C. Then, 136 g (0.41 mol) of 2,4,6-tribromophenol was added and dissolved. After cooling, the tribromophenolate solution (concentration of TBP=48%) thus obtained was added dropwise to the above cyanuric chloride solution at a temperature of 3–30° C. After completion of the dropwise addition, the reaction mixture was aged under reflux for 30 minutes. After aging, the methylene chloride was distilled off at atmospheric pressure.

The product was recovered by filtration and dried to provide white crystals of tris(tribromophenoxy)-s-triazine.

The results are shown in Table 3.

TABLE 3

|  | Example 5 | Example 6 | Example 7 | Comparative Example 4 |
|---|---|---|---|---|
| Yield (g) | 281.1 | 280.9 | 283.2 | 124.2 |
| Yield (%) | 97 | 97 | 98 | 86 |
| Melting point (° C.) | 230.0 | 230.0 | 230.4 | 219.3 |
| Heat resistance (APHA)* | 70 | 60 | 60 | 500 |
| Output per unit reactor capacity (w/v %) | 56.2 | 56.2 | 56.8 | 24.8 |

*See Table 2.

EXAMPLE 8

A 500 ml reactor equipped with a stirrer, condenser, thermometer and drip funnel was charged with 130 g of methylene chloride and 20 g (0.108 mol) of cyanuric chloride, followed by addition of 0.6 g of triphenylethylphosphonium bromide to the resulting solution or dispersion.

Another 500 ml reactor equipped with a stirrer, condenser and thermometer was charged with 130 g of water and 13.6 g (0.34 mol) of sodium hydroxide and the solution was cooled to a temperature not exceeding 10° C. Then, 110 g (0.33 mol) of 2,4,6-tribromophenol was added. After the resulting solution was cooled, 0.07 g of triethylamine was added. The tribromophenolate solution (concentration of TBP=46%) thus obtained was added dropwise to the above cyanuric chloride solution at a temperature of 3–30° C. After completion of the dropwise addition, the reaction mixture was aged at 25° C.

The reaction mixture was sampled at completion of dropwise addition (0.0 hour) and after 0.5 hour, 1.0 hour, 1.5 hours, 2.0 hours and 2.5 hours of aging. Each sample was poured in methanol and the precipitate was recovered by filtration and dried. The melting point was then measured with a Mettler melting point apparatus.

The results are shown in Table 4.

COMPARATIVE EXAMPLE 5

A 500 ml reactor equipped with a stirrer, condenser, thermometer and drip funnel was charged with 130 g of methylene chloride and 20 g (0.108 mol) of cyanuric chloride, followed by addition of 0.6 g of triphenylethylphosphonium bromide to the resulting solution or dispersion.

Another 500 ml reactor equipped with a stirrer, condenser and thermometer was charged with 130 g of water and 13.6 g (0.34 mol) of sodium hydroxide and the solution was cooled to a temperature not exceeding 10° C. Then, 110 g (0.33 mol) of 2,4,6-tribromophenol was added and dissolved. After cooling, the tribromophenolate solution (concentration of TBP=46%) thus obtained was added dropwise to the above cyanuric chloride solution at a temperature of 3–30° C. After completion of the dropwise addition, the reaction mixture was aged at 25° C.

The reaction mixture was sampled at completion of dropwise addition (0.0 hour) and after 0.5 hour, 1.0 hour, 1.5 hours, 2.0 hours and 2.5 hours of aging. Each sample was poured in methanol and the precipitate was recovered by filtration and dried. The melting point was then measured with a Mettler melting point apparatus.

The results are shown in Table 4.

COMPARATIVE EXAMPLE 6

A 500 ml reactor equipped with a stirrer, condenser, thermometer and drip funnel was charged with 130 g of methylene chloride and 20 g (0.108 mol) of cyanuric chloride, followed by addition of 0.6 g of triphenylethylphosphonium bromide to the resulting solution or dispersion.

Another 500 ml reactor equipped with a stirrer, condenser and thermometer was charged with 130 g of water and 13.6 g (0.34 mol) of sodium hydroxide and the solution was cooled to a temperature not exceeding 10° C. Then, 110 g (0.33 mol) of 2,4,6-tribromophenol was added and dissolved. After cooling, the tribromophenolate solution (concentration of TBP=46%) thus obtained was added dropwise to the above cyanuric chloride solution at a temperature of 3–30° C. After completion of the dropwise addition, the reaction mixture was aged at 25° C. for 30 minutes and, then, under reflux.

The reaction mixture was sampled at completion of dropwise addition (0.0 hour) and after 0.5 hour, 1.0 hour, 1.5 hours, 2.0 hours and 2.5 hours of aging. Each sample was poured in methanol and the precipitate was recovered by filtration and dried. The melting point was then measured with a Mettler melting point apparatus.

The results are shown in Table 4.

COMPARATIVE EXAMPLE 7

A 500 ml reactor equipped with a stirrer, condenser, thermometer and drip funnel was charged with 130 g of methylene chloride and 20 g (0.108 mol) of cyanuric chloride, followed by addition of 1.0 g of triphenylethylphosphonium bromide to the resulting solution or dispersion.

Another 500 ml reactor equipped with a stirrer, condenser and thermometer was charged with 130 g of water and 13.6 g (0.34 mol) of sodium hydroxide and the solution was cooled to a temperature not exceeding 10° C. Then, 110 g (0.33 mol) of 2,4,6-tribromophenol was added and dissolved. After cooling, the tribromophenolate solution (concentration of TBP=46%) thus obtained was added dropwise to the above cyanuric chloride solution at a temperature of 3° C.'—reflux temperature. After completion of the dropwise addition, the reaction mixture was aged.

The reaction mixture was sampled at completion of dropwise addition (0.0 hour) and after 0.5 hour, 1.0 hour, 1.5 hours, 2.0 hours and 2.5 hours of aging. Each sample was poured in methanol and the precipitate was recovered by filtration and dried. The melting point was then measured with a Mettler melting point apparatus.

The results are shown in Table 4.

TABLE 4

| | | Melting point (° C.) Aging time (Hr) | | | | | |
|---|---|---|---|---|---|---|---|
| | | 0.0 | 0.5 | 1.0 | 1.5 | 2.0 | 2.5 |
| Example 8 | | 230 | 231 | 231 | 231 | 231 | 231 |
| Comparative | 5 | 219 | 220 | 216 | 198 | 226 | 229 |

TABLE 4-continued

| | | Melting point (° C.) Aging time (Hr) | | | | | |
|---|---|---|---|---|---|---|---|
| | | 0.0 | 0.5 | 1.0 | 1.5 | 2.0 | 2.5 |
| Example | 6 | 221 | 218 | 216 | 218 | 220 | 227 |
| | 7 | 219 | 210 | 212 | 212 | 218 | 225 |

EXAMPLE 9

A 500 ml reactor equipped with a stirrer, condenser, thermometer and drip funnel was charged with 160 g of methylene chloride and 25 g (0.136 mol) of cyanuric chloride, followed by addition of 0.8 g of triethylbenzylammonium chloride to the resulting solution or dispersion.

Another 500 ml reactor equipped with a stirrer, condenser and thermometer was charged with 150 g of water and 17.1 g (0.43 mol) of sodium hydroxide and the solution was cooled to a temperature not exceeding 10° C. Then, 136 g (0.41 mol) of 2,4,6-tribromophenol was added and dissolved. After the resulting solution was cooled, 0.1 g of triethylamine was added. The tribromophenolate solution (concentration of TBP=48%) thus obtained was added dropwise to the above cyanuric chloride solution at a temperature of 3–30° C. After completion of the dropwise addition, the reaction mixture was aged at 25° C. for 30 minutes. After aging, the methylene chloride was distilled off at atmospheric pressure.

The product was recovered by filtration and dried to provide white crystals of tris(tribromophenoxy)-s-triazine.

The results are shown in Table 5.

EXAMPLE 10

A 500 ml reactor equipped with a stirrer, condenser, thermometer and drip funnel was charged with 160 g of methylene chloride and 25 g (0.136 mol) of cyanuric chloride, followed by addition of 0.8 g of triethylbenzylammonium chloride to the resulting solution or dispersion.

Another 500 ml reactor equipped with a stirrer, condenser and thermometer was charged with 150 g of water, 17.1 g (0.43 mol) of sodium hydroxide and 0.07 g of sodium sulfite and the solution was cooled to a temperature not exceeding 10° C. Then, 136 g (0.41 mol) of 2,4,6-tribromophenol was added and dissolved. After the resulting solution was cooled, 0.1 g of triethylamine was added. The tribromophenolate solution (concentration of TBP=48%) thus obtained was added dropwise to the above cyanuric chloride solution at a temperature of 3–30° C. After completion of the dropwise addition, the reaction mixture was aged at 25° C. for 30 minutes. After aging, the methylene chloride was distilled off at atmospheric pressure.

The product was recovered by filtration and dried to provide white crystals of tris(tribromophenoxy)-s-triazine.

The results are shown in Table 5.

EXAMPLE 11

A 500 ml reactor equipped with a stirrer, condenser and thermometer was charged with 150 g of water, 17.1 g (0.43 mol) of sodium hydroxide and 0.07 g of sodium sulfite and the solution was cooled to a temperature not exceeding 10° C. Then, 136 g (0.41 mol) of 2,4,6-tribromophenol was added and dissolved. After the resulting solution was cooled, 0.8 g of ethylbenzylammonium chloride, 0.1 g of triethylamine and 160 g of methylene chloride were added. To the tribromophenolate solution (concentration of TBP=48%) thus obtained was added 25 g (0.136 mol) of cyanuric chloride powder at a reaction temperature of 3–30° C. After completion of the addition, the reaction mixture was aged at 25° C. for 30 minutes. After aging, the methylene chloride was distilled off at atmospheric pressure.

The product was recovered by filtration and dried to provide white crystals of tris(tribromophenoxy)-s-triazine.

The results are shown in Table 5.

COMPARATIVE EXAMPLE 8

A 500 ml reactor equipped with a stirrer, condenser, thermometer and drip funnel was charged with 160 g of methylene chloride and 25 g (0.136 mol) of cyanuric chloride, followed by addition of 0.8 g of triethylbenzylammonium chloride to the resulting solution or dispersion.

Another 500 ml reactor equipped with a stirrer, condenser and thermometer was charged with 150 g of water and 17.1 g (0.43 mol) of sodium hydroxide and the solution was cooled to a temperature not exceeding 10° C. Then, 136 g (0.41 mol) of 2,4,6-tribromophenol was added and dissolved. After cooling, the tribromophenolate solution (concentration of TBP=48%) thus obtained was added dropwise to the above cyanuric chloride solution at a temperature of 3–30° C. After completion of the dropwise addition, the reaction mixture was aged at 25° C. for 30 minutes. After aging, the methylene chloride was distilled off at atmospheric pressure.

The product was recovered by filtration and dried to provide white crystals of tris(tribromophenoxy)-s-triazine.

The results are shown in Table 5.

TABLE 5

| | Example 9 | Example 10 | Example 11 | Comparative Example 8 |
|---|---|---|---|---|
| Yield (g) | 138.9 | 140.5 | 140.6 | 127.3 |
| Yield (%) | 96 | 97 | 97 | 88 |
| Melting point (° C.) | 230.0 | 230.0 | 230.2 | 220.2 |
| Heat resistance (APHA)* | 80 | 70 | 60 | 500 |

*See Table 2.

EXAMPLE 12

A 500 ml reactor equipped with a stirrer, condenser, thermometer and drip funnel was charged with 150 g of methylene chloride and 50 g (0.271 mol) of cyanuric chloride, followed by addition of 1.6 g of tetrabutylammonium bromide to the resulting solution or dispersion.

Another 500 ml reactor equipped with a stirrer, condenser and thermometer was charged with 96 g of water and 34.2 g (0.86 mol) of sodium hydroxide and the solution was cooled to a temperature not exceeding 10° C. Then, 130 g of methylene chloride, e.g. reaction solvent, and 272 g (0.82 mol) of 2,4,6-tribromophenol were added and dissolved. After the resulting solution was cooled, 0.2 g of triethylamine was added. The tribromophenolate solution (concentration of TBP=74%) thus obtained was added dropwise to the above cyanuric chloride solution at a temperature of 3–30° C. After completion of the dropwise addition, the reaction mixture was aged at 25° C. for 30 minutes. After aging, the methylene chloride was distilled off at atmospheric pressure.

The product was recovered by filtration and dried to provide white crystals of tris(tribromophenoxy)-s-triazine.

The results are shown in Table 6.

EXAMPLE 13

A 500 ml reactor equipped with a stirrer, condenser, thermometer and drip funnel was charged with 150 g of methylene chloride and 50 g (0.271 mol) of cyanuric chloride, followed by addition of 1.6 g of tetrabutylammonium bromide to the resulting solution or dispersion.

Another 500 ml reactor equipped with a stirrer, condenser and thermometer was charged with 96 g of water, 34.2 g (0.86 mol) of sodium hydroxide and 0.14 g of sodium sulfite and the solution was cooled to a temperature not exceeding 10° C. Then, 130 g of methylene chloride, e.g. reaction solvent, and 272 g (0.82 mol) of 2,4,6-tribromophenol were added and dissolved. After the resulting solution was cooled, 0.2 g of triethylamine was added. The tribromophenolate solution (concentration of TBP=74%) thus obtained was added dropwise to the above cyanuric chloride solution at a temperature of 3–30° C. After completion of the dropwise addition, the reaction mixture was aged at 25° C. for 30 minutes. After aging, the methylene chloride was distilled off at atmospheric pressure.

The product was recovered by filtration and dried to provide white crystals of tris(tribromophenoxy)-s-triazine.

The results are shown in Table 6.

EXAMPLE 14

A 500 ml reactor equipped with a stirrer, condenser and thermometer was charged with 96 g of water, 34.2 g (0.86 mol) of sodium hydroxide and 0.14 g of sodium sulfite and the solution was cooled to a temperature not exceeding 10° C. Then, 130 g of methylene chloride, e.g. reaction solvent, and 272 g (0.82 mol) of 2,4,6-tribromophenol were added and dissolved. After the resulting solution was cooled, 1.6 g of tetrabutylammonium bromide, 0.2 g of triethylamine and 150 g of methylene chloride were added. To the tribromophenolate solution (concentration of TBP=74%) thus obtained was added 50 g (0.271 mol) of cyanuric chloride powder at a reaction temperature of 3–30° C. After completion of the addition, the reaction mixture was aged at 25° C. for 30 minutes. After aging, the methylene chloride was distilled off at atmospheric pressure.

The product was recovered by filtration and dried to provide white crystals of tris(tribromophenoxy)-s-triazine.

The results are shown in Table 6.

COMPARATIVE EXAMPLE 9

A 500 ml reactor equipped with a stirrer, condenser, thermometer and drip funnel was charged with 160 g of methylene chloride and 25 g (0.136 mol) of cyanuric chloride, followed by addition of 0.8 g of tetrabutylammonium bromide to the resulting solution or dispersion.

Another 500 ml reactor equipped with a stirrer, condenser and thermometer was charged with 150 g of water and 17.1 g (0.43 mol) of sodium hydroxide and the solution was cooled to a temperature not exceeding 10° C. Then, 136 g (0.41 mol) of 2,4,6-tribromophenol was added and dissolved. After cooling, the tribromophenolate solution (concentration of TBP=48%) thus obtained was added dropwise to the above cyanuric chloride solution at a temperature of 3–30° C. After completion of the dropwise addition, the reaction mixture was aged at 25° C. for 30 minutes. After aging, the methylene chloride was distilled off at atmospheric pressure.

The product was recovered by filtration and dried to provide white crystals of tris(tribromophenoxy)-s-triazine.

The results are shown in Table 6.

TABLE 6

|  | Example 12 | Example 13 | Example 14 | Comparative Example 9 |
|---|---|---|---|---|
| Yield (g) | 277.6 | 278.0 | 280.9 | 128.7 |
| Yield (%) | 96 | 96 | 97 | 89 |
| Melting point (° C.) | 230.0 | 230.0 | 230.2 | 219.2 |
| Heat resistance (APHA)* | 70 | 60 | 60 | 500 |
| Output per unit reactor capacity (w/v %) | 55.6 | 55.6 | 56.2 | 25.4 |

*See Table 2.

What is claimed is:

1. A process for producing tris(tribromophenoxy)-s-triazine which comprises subjecting cyanuric chloride and an aqueous tribromophenolate solution with concentration of not less than 50% and containing a reducing agent to reaction in the presence of a phase transfer catalyst.

2. A process for producing tris(tribromophenoxy)-s-triazine which comprises subjecting cyanuric chloride and an aqueous tribromophenolate solution to reaction in the presence of a tertiary amine.

3. The process according to claim 1 or 2 wherein said cyanuric chloride is subjected to reaction in the form of a solution or dispersion in a non-hydrophilic solvent.

* * * * *